Nov. 29, 1938. L. MAILLOCHON ET AL Plant Pat. 306
PEACH TREE
Filed July 13, 1937
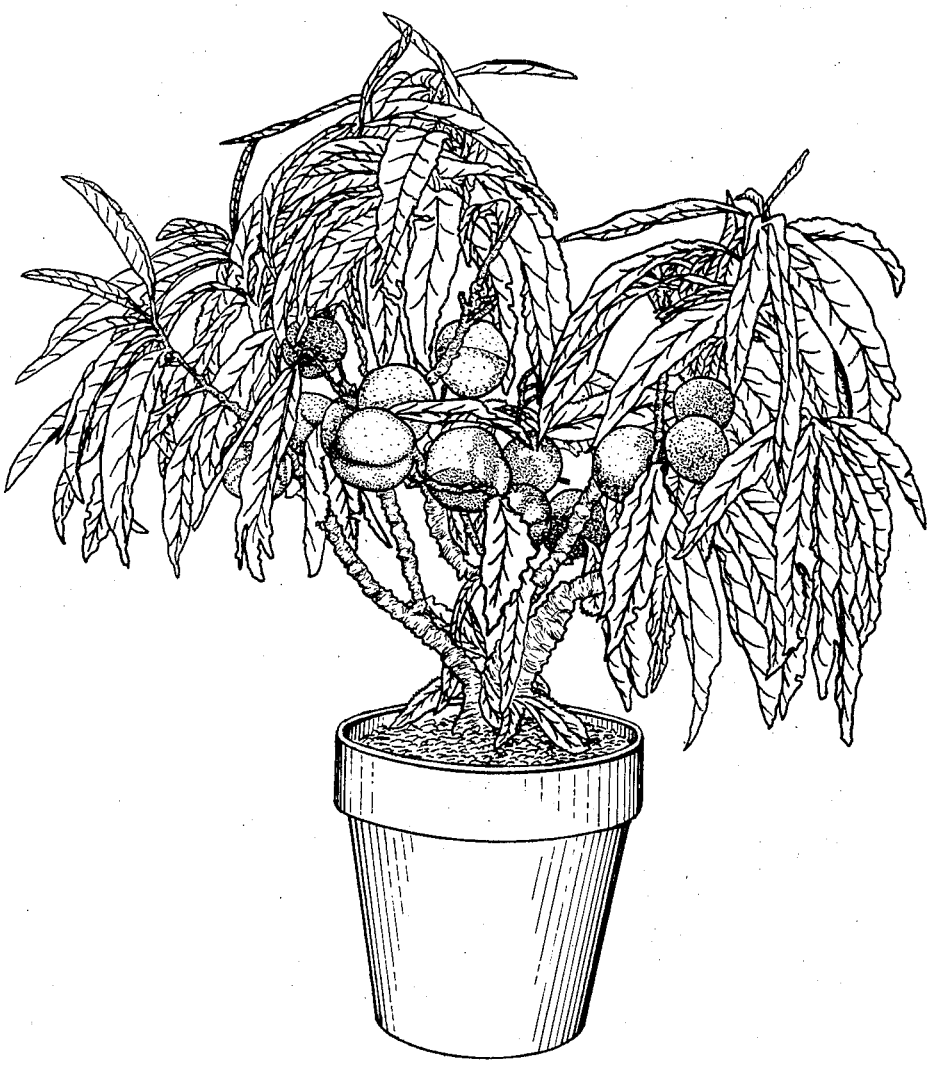
Inventor
L. Maillochon
E. Martaud
By Robb & Robb
Attorneys Patented Nov. 29, 1938

Plant Pat. 306

UNITED STATES PATENT OFFICE

306

PEACH TREE

Léon Maillochon and Ernest Marlaud, Argenton-sur-Creuse (Indre), France, assignors to Stark Bro's Nurseries & Orchards Company, Louisiana, Mo.

Application July 13, 1937, Serial No. 153,434

1 Claim. (Cl. 47—62)

The present discovery relates to a new and distinct variety of peach tree, a seedling variation, the novel characteristics of which reside in its dwarfish growth and the unusual habit, in a dwarf variety, of the production of both blooms and edible fruit.

This new peach was discovered incident to the sowing of a group of common peach-stones for the purpose of securing stock for budding and grafting. Amongst this group was noticed one plant which was only ten centimeters high whereas the others were a meter high. On this original and distinct plant there were three peaches the third year, and it has borne fruit every year since.

The tree or shrub and its progeny appear to grow about thirty centimeters every year, reaching a maximum height of eighty centimeters. The illustration in the original drawing shows the size of a mature specimen of this plant, in comparison with a flower pot.

The new variety is found to possess considerable value because of its adaptation for garden decoration and in view of the fact that it may be grown in a pot and can be forced, the plant presents great interest from the decorative point of view because of its gorgeous flowering effect.

In the development of the plant, we have found that it carries out its dwarf characteristics when budded on other stocks, and reproductions from the original come true to type, bearing blooms which appear before the leaves and fruit. It has been noted that young trees in nursery row bloomed when only eight inches high.

The following is a brief description of this new variety, color terminology being in accordance with the ordinary dictionary definitions.

Due to short stubby habit of growth of the tree, blooms are formed close together on last season's wood and are abundant.

Bloom itself is borne on very short stem.

Five and sometimes six sepals about three-sixteenths of an inch long, red in color on the outside, pale green inside. Flower very similar to regular peach blossom. Somewhat cupped when first opening, later almost flat. Diameter of flower about one and one-half inches.

Five and sometimes six petals varying in size, usually about five-eighths of an inch long and about one-half inch wide. Color of petals a deep pink as flower opens, fading to very light pink, almost white. Single row of petals.

Style is fairly long, about one-half inch. Nearly one-fourth of an inch longer than the stamens.

The flowers are numerous and have no fragrance.

Petals seem to hang well and flowers being of large petal type are more resistant to frost than the Elberta type of peach bloom.

The leaves show as rosette terminals and in treating the leaves in part we have obtained on the fruit a rather bright coloring. The leaves are wide and waved and without glands.

The fruit is spheric in shape with shallow groove, normally green yellowish with white meat, greenish brittle and with free stone small in size, oval-shaped and very arched, its medium weight being one hundred grams.

The fruit when over-ripe is more or less sugared, very refreshing and has somewhat the taste of fresh figs.

Supplementing the foregoing, it may be noted that this new variety distinctly differs as to vegetation and fruiting from the Dwarf Orleans originated in France about 1715 of which only a few specimens are to be found in collections of today. The said shrub shows a height of 1 meter to the short branches, whereas the new variety does not exceed 0.60 centimeter to the same point. The branches are thickly set, stubby with no internodes. The leaves are large, wide and waved. The fruit is globular with shallow suture as above noted, whereas in the Orleans this groove is deep and the flowers are rose color. The fruit of the Orleans also has a thready, acidulated flesh and ripens about one month later than the present variety.

We claim:

A new and distinct variety of peach tree, substantially as shown and described, characterized by its dwarfish growth and the production of attractive blooms, followed by leaves and edible fruit.

LÉON MAILLOCHON.
ERNEST MARLAUD.